US010688139B2

(12) United States Patent
Breton et al.

(10) Patent No.: US 10,688,139 B2
(45) Date of Patent: *Jun. 23, 2020

(54) ORALLY ADMINISTRABLE COMPOSITION FOR THE PHOTOPROTECTION OF THE SKIN

(75) Inventors: Lionel Breton, Versailles (FR); Isabelle Bureau-Franz, Morges (CH); Chantal Fanchon, Paris (FR)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 1665 days.

This patent is subject to a terminal disclaimer.

(21) Appl. No.: 11/772,704

(22) Filed: Jul. 2, 2007

(65) Prior Publication Data
US 2007/0280999 A1    Dec. 6, 2007

Related U.S. Application Data

(62) Division of application No. 10/505,305, filed as application No. PCT/EP03/01685 on Feb. 18, 2003, now abandoned.

(30) Foreign Application Priority Data

Feb. 21, 2002   (EP) ..................... 02075703

(51) Int. Cl.
A61K 35/747     (2015.01)
A61K 8/99       (2017.01)
A61Q 17/04      (2006.01)
A61K 8/31       (2006.01)
A61K 36/062     (2006.01)
A61K 31/015     (2006.01)
A61K 31/07      (2006.01)
A61K 35/745     (2015.01)

(52) U.S. Cl.
CPC .............. A61K 35/747 (2013.01); A61K 8/31 (2013.01); A61K 8/99 (2013.01); A61K 31/015 (2013.01); A61K 31/07 (2013.01); A61K 36/062 (2013.01); A61Q 17/04 (2013.01); A61K 35/745 (2013.01); A61K 2800/92 (2013.01)

(58) Field of Classification Search
CPC ...... A61K 35/747; A61K 8/31; A61K 36/062; A61K 31/015; A61K 31/07; A61K 8/99; A61K 2800/92; A61K 35/745; A61Q 17/04

See application file for complete search history.

(56) References Cited

U.S. PATENT DOCUMENTS

| 3,920,834 | A | 11/1975 | Klaui et al. |
| 4,464,362 | A | 8/1984 | Kludas et al. |
| 4,646,362 | A | 3/1987 | Heran et al. |
| 4,806,368 | A | 2/1989 | Reddy |
| 5,192,565 | A | 3/1993 | Buhler et al. |
| 5,397,773 | A | 3/1995 | Donzis |
| 5,501,857 | A | 3/1996 | Zimmer |
| 5,603,930 | A | 2/1997 | Brassart et al. |
| 6,030,650 | A | 2/2000 | Kamarei |
| 6,110,478 | A | 8/2000 | Harang |
| 6,156,355 | A | 12/2000 | Shields et al. |
| 6,254,886 | B1 | 7/2001 | Fusca et al. |
| 7,037,708 | B1 | 5/2006 | Runge et al. |
| 7,547,527 | B2 * | 6/2009 | Baur ................ A61K 8/99 424/184.1 |
| 2003/0059501 | A1 | 3/2003 | Rivier |
| 2004/0013732 | A1 | 1/2004 | Farber et al. |
| 2005/0158291 | A1 | 7/2005 | Breton |

FOREIGN PATENT DOCUMENTS

| EP | 0 931 543 | 7/1999 |
| EP | 1 222 919 | 5/2008 |
| FR | 2 698 268 | 5/1994 |
| FR | 2 718 752 | 10/1995 |
| FR | 2 725 896 | 4/1996 |
| WO | WO 96/26732 | 9/1996 |
| WO | WO 00/33854 | 6/2000 |
| WO | WO 01/45721 | * 6/2001 |

OTHER PUBLICATIONS

WO 01/45721. Jun. 2001. Machine Translation. (Year: 2001).*
Reeve, M. et al., "Differential by Two Suncreens From UV Radiation—Induced Immunosuppression," J Invest Dermatol., vol. 97, No. 4, pp. 624-628 (1991).
One Look Dictionary Search—definition of food. www.onelook.com (2006).

* cited by examiner

Primary Examiner — Susan E. Fernandez
(74) Attorney, Agent, or Firm — K&L Gates LLP

(57) ABSTRACT

An orally administrable composition for the photoprotection of the skin which comprises the combination of i) at least one probiotic lactic acid bacterium or a culture supernatant thereof, and ii) at least one carotenoid or derivative, included into an orally acceptable carrier.

9 Claims, No Drawings

ORALLY ADMINISTRABLE COMPOSITION FOR THE PHOTOPROTECTION OF THE SKIN

PRIORITY CLAIM

This is a divisional of U.S. patent application Ser. No. 10/505,305 filed on Oct. 27, 2004 entitled "ORALLY ADMINISTRABLE COMPOSITION FOR THE PHOTOPROTECTION OF THE SKIN"; which is a U.S. national stage application under 35 U.S.C. § 371 of PCT/EP03/01685 filed on Feb. 18, 2003, the entire disclosure of which is hereby incorporated by reference.

FIELD OF THE INVENTION

The present invention relates to orally administrable composition or pharmaceutical compositions, or cosmetical compositions, for the protection of the skin against negative effects from the environment, in particular exposure to solar radiation, which is orally administrable, and a method to improve the photoprotection of the skin.

BACKGROUND

The continuous decrease of the atmosphere's ozone layer with the concurrent increase of ultraviolet radiation reaching the planet's surface has attracted a great deal of interest in its potential consequence on human health. Although exposure to ultraviolet radiation is needed for humans to produce vitamin D, growing evidence suggests that extensive exposure to sun-light, in particular to ultraviolet radiation, causes a variety of problems in the skin, including induction of certain skin cancers and induction of accelerated skin ageing.

In addition to these established health concerns, research has also provided evidence suggesting that exposure to ultraviolet radiation may negatively affect a variety of immune responses in living beings both locally, within the UV-irradiated skin, and also systemically, i.e. at sites distant from the irradiated skin.

It is thus important to alleviate the detrimental effects of ultraviolet radiation on the skin, and also prevent the development of erythema, oedema and/or flaking or scaling (hyperkeratosis) of the skin.

In the art, there have been several attempts, such as by using sunscreens or other particular pharmacological agents.

In J. Invest. Dermatol., 97 (1991), 624-628 it is reported that topical application of ultraviolet radiation-absorbing compounds (sunscreens) is effective in preventing ultraviolet radiation-induced erythema and edema but cannot prevent UV-light induced immuno-suppression. This finding was confirmed by several other studies, according to which sunscreens seems to prevent inflammation or irritation but do not provide complete prophylactic protection against the immuno-suppressive effects of ultraviolet radiation.

On the other hand, In FR 2698 268 (L'Oreal) an orally administrable composition comprising a combination of at least one amino-acid, salt of copper and a mix of vitamins has been shown to protect the skin against ultraviolet radiation.

However, there is still a need in the art for an orally administrable composition, which is capable to improve and/or reinforce the photoprotective function of the skin.

SUMMARY

Accordingly, in a first aspect the present invention aims to provide an orally administrable composition for the photoprotection of the skin which comprises a photoprotecting effective amount of i) at least one probiotic lactic acid bacterium or a culture supernatant thereof, and ii) at least one carotenoid or derivative, included into an orally acceptable carrier.

The present invention further relates to the use of a photoprotecting effective amount of at least one probiotic lactic acid bacterium or a culture supernatant thereof and at least one carotenoid, included into an orally acceptable carrier for preparing an orally administrable composition for protecting the skin against solar radiations such as ultraviolet and all related skin disorders, such as erythema, inflammation, sun burn, barrier function, photoageing, alteration of the immune system, for example.

In a last aspect, the invention relates to a method for improving the photoprotective function of the skin, which comprises the step of orally administering to the individual a composition comprising a photoprotecting effective amount of i) at least one probiotic lactic acid bacterium or a culture supernatant thereof, and ii) at least one carotenoid or derivative, in an orally acceptable carrier.

The combination according to the present invention has a particular beneficial effect on skin protection and coloration of the skin that helps to reduce the effects of solar radiation-related stress on skin.

Additional features and advantages are described herein, and will be apparent from, the following Detailed Description and the FIGURES.

DETAILED DESCRIPTION

Within the following description, "NCC" designates Nestle Culture Collection (Nestlé Research Center, Verschez-les-Blanc, Lausanne, Switzerland). The term "photoprotection" is used to describe attempt to block or reduce the adverse clinical, histological and immunological effects of solar radiation exposure on the skin.

According to the present invention, the subject compositions comprise, as the active agents therefor, combinatory mixture of at least one probiotic lactic acid bacterium or a culture supernatant thereof, and at least one carotenoid or derivative.

Indeed, it has now surprisingly and unexpectedly been determined that admixture of these two very specific constituents elicits an enhanced effect or response in respect of the photoprotection of the skin.

Probiotics are non-pathogenic and non-toxigenic organisms that survive passage through the stomach and small intestine. Upon continuous ingestion by the host they eventually may colonize the gut to a substantial extent thus competing with other potentially pathogenic bacteria for nutrients and/or attachment sites on the gastro-intestinal wall and reducing their numbers and reducing or preventing infections. Until now a number of different probiotic microorganisms have been found, which all are reported to exert their effect in the gut via the production of toxins, metabolic by-products, short chain fatty acids and the like.

It has now been shown that probiotics do also exert an effect in an individual's body at a location distant from the region in which they colonize it. And particularly, it has been surprisingly found that a composition having a synergistic photoprotective effect on the skin may be obtained by combining into an orally acceptable carrier, a probiotic microorganism and an active compound such as carotenoid.

In a preferred embodiment, the probiotic to be included into the carrier is selected from the group consisting of lactic acid bacteria, in particular Lactobacilli and/or Bifidobacteria and are more preferably *Lactobacillus johnsonii, Lactobacillus reuteri, Lactobacillus rhamnosus, Lactobacillus paracasei, Lactobacillus casei* or *Bifidobacterium bifidum, Bifidobacterium breve, Bifidobacterium longum, Bifidobacterium animalis, Bifidobacterium lactis, Bifidobacterium infantis, Bifidobacterium adolescentis, Bifidobacterium pseudocatenulatum*, or a mixture thereof.

According to a most preferred embodiment the strains *Lactobacillus johnsonii* NCC 533, *Lactobacillus paracasei* NCC 2461, *Bifidobacterium adolescentis* NCC 251 and *Bifidobacterium longum* NCC 490 were deposited by way of an example, under the Budapest Treaty with the Institut Pasteur (28 rue du Docteur Roux, F-75024 Paris cédex 15) on 30.06.92, 12.01.99, 15.04.99 and 15.03.99, respectively and under the deposit number CNCM I-1225, CNCM I-2116, CNCM I-2168 and CNCM I-2170, respectively.

The strain of *Bifidobacterium lactis* (ATCC27536) provided by Hansen (Chr. Hansen A/S, 10-12 Boege Alle, P.O. Box 407, DK-2970 Hoersholm, Danemark) can also be used.

The probiotic microorganism according to the present invention may be included in a live form, dead form, semi-active or in deactivated form and fragments or fractions originating from the microorganism either live or dead e.g. as a lyophilized powder. Also culture supernatants of the microorganisms may be included in the products, optionally in concentrated form. It may also be included in an encapsulated form. When using a supernatant of a probiotic's culture the supernatant may be used as such or may be subjected to one or more purification steps prior to inclusion into the product, so as to concentrate or isolate the active ingredient (s)/metabolite (s). Method and techniques for purifying compounds and detecting the activity thereof in the fractions obtained are well known to the skilled person.

The probiotic lactic acid bacteria may be present in the carrier in an amount of at least $10^5$ cfu/g of carrier and preferably from about $10^5$ to $10^{15}$ cfu/g of orally acceptable carrier, and more preferably from $10^7$ to $10^{12}$ cfu/g of orally acceptable carrier.

The carotenoid may be a carotenoid with or without provitamin A activity. It may be β-carotene, γ-carotene, α-carotene, lycopene, zeaxanthine and luteine, or a mixture thereof. The carotenoid may be from synthetic or natural origin or contained in a natural extract. When the carotenoid is from natural origin, it is preferably obtained from plant material, in which the plant is grown in-vivo or in-vitro. Method for extracting the carotenoids is well known in the art. The carotenoid may be present in the carrier in an amount of from $10^{-12}$% to 20% by weight and preferably from 0,00001 mg to 50 mg/day and more preferably from 0.001 mg to 30 mg/day.

A mixture of a plurality of lactic acid bacteria or carotenoids may also be used.

The carrier may be any food or pharmaceutical product, or a nutritional supplement for oral administration or a composition for oral administration, wherein the probiotic microorganism and the carotenoid may be included. Examples for food or pharmaceuticals carriers are milk, yoghurt, curd, cheese, fermented milks, milk based fermented products, ice-creams, fermented cereal based products, milk based powders, infant formulae or tablets, liquid suspensions, dried oral supplement, wet oral supplement, dry-tube-feeding. The nutritionally supplement for oral administration may be in capsules, soft capsules, tablets, pastes or pastilles, gums, or drinkable solutions or emulsions. Methods for preparing the carrier are common knowledge.

The composition according to the invention may further comprise bioactive molecules or yeast extracts, for example. In a preferred embodiment, the yeast is any food-grade yeast selected from the group consisting of Ascomycotina or Deuteromycotina. In a preferred embodiment, the yeast may be selected from the group consisting of *Debaryomyces, Kluyveromyces, Saccharomyces, Yarrowia, Zygosaccharomyces, Candida* and *Rhodutorula*, and more preferably *Saccharomyces* caerevisae (baker's yeast).

Such yeast may be used in the form of dried or lyophilized extracts. It may be present in the carrier in an amount of at least $10^5$ cfu/g of orally acceptable carrier, preferably from about $10^5$ to $10^{15}$ cfu/g of orally acceptable carrier, and more preferably from $10^7$ to $10^{12}$ cfu/g of orally acceptable carrier, said amount depending on the nature and activity of the particular yeast.

The composition according to the invention may also comprise usual excipients, in particular sweeteners, flavouring agents or preservatives.

The composition according to the invention provides a surprising and synergistic protective and preventive effect of the skin.

Accordingly, in another aspect, the invention relates to a method for improving the photoprotective function of the skin, which comprises the step of orally administering to an individual a composition comprising a photoprotecting effective amount of i) at least one probiotic lactic acid bacterium or a culture supernatant thereof, and ii) at least one carotenoid or derivative, in an orally acceptable carrier.

The amount of the composition to be consumed by the individual will depend on the desirable effect. However, an amount of the composition to provide a daily amount of about $10^5$ to $10^{15}$ organisms, which organism may be alive or dead, and from 0,00001 mg to 50 mg of carotenoids, would usually are adequate.

The composition is administered to an individual before or during the exposure to ultraviolet radiation, in particular exposure to sun. When the exposure period is foreseeable, it is desirable to start the consumption before the exposure and preferably 1 to 2 months before, and to prolong consumption during exposure.

The following examples are given by way of illustration only and in no way should be construed as limiting the subject matter of the present application. All percentages are given by weight unless otherwise indicated.

EXAMPLES

In the following examples 1 to 6, β-carotene is provided by Roche, Lycopene is provided by Lycored, Lyophilized *S. cerevissae* is provided by BioSpringer, *Latobacillus* CNCM I-1225 dry mix, *Lactobacillus* CNCM I-2116 or *Bifidobacterium* CNCM I-2168 dry mix are prepared so that they contain $1.10^8$ to $1.10^9$ organisms.

Example 1

A photoprotective daily orally administrable composition is prepared as follows:

| | |
|---|---:|
| β-carotene (Roche) | 4.7 mg |
| *Latobacillus* CNCM I-1225 dry mix | 50 mg |
| Glucidex IT 19 (maltodextrin powder) | QSP 500 mg |

The composition is administered to the individual in an amount of 2×500 mg daily, which provides a protective and preventive effect of the skin.

Example 2

A photoprotective daily orally administrable composition is prepared as follows:

| | |
|---|---:|
| β-carotene | 4.7 mg |
| *Zeaxanthine* | 10 mg |
| *Latobacillus* CNCM I-1225 dry mix | 50 mg |
| Glucidex IT 19 (maltodextrin powder) | QSP 500 mg |

The composition is administered to the individual in an amount of 2×500 mg daily, which provides a protective and preventive effect of the skin.

Example 3

A photoprotective daily orally administrable composition is prepared as follows:

| | |
|---|---:|
| β-carotene | 4.7 mg |
| *Lycopene* | 2.5 mg |
| *Bifidobacterium* CNCM I-2168 | 30 mg |
| *Latobacillus* CNCM I-1225 dry mix | 30 mg |
| Glucidex IT 19 (maltodextrin powder) | QSP 500 mg |

The composition is administered to the individual in an amount of 2×500 mg daily, which provides a protective and preventive effect of the skin.

Example 4

A photoprotective daily orally administrable composition is prepared as follows:

| | |
|---|---:|
| *Lycopene* | 2.5 mg |
| Lyophilized *S. cerevissae* | 75 mg |
| *Latobacillus* CNCM I-2116 dry mix | 50 mg |
| Glucidex IT 19 (maltodextrin powder) | QSP 500 mg |

The composition is administered to the individual in an amount of 2×500 mg daily, which provides a protective and preventive effect of the skin.

Example 5

A photoprotective daily orally administrable composition is prepared as follows:

| | |
|---|---:|
| β-carotene | 4.7 mg |
| *Lycopene* | 2.5 mg |
| Lyophilized *S. cerevissae* | 75 mg |
| *Latobacillus* CNCM I-1225 dry mix | 50 mg |
| Glucidex IT 19 (maltodextrin powder) | QSP 500 mg |

The composition is administered to the individual in an amount of 2×500 mg daily, which provides a protective and preventive effect of the skin.

Example 6

A photoprotective daily orally administrable composition is prepared as follows:

| | |
|---|---:|
| β-carotene | 4.7 mg |
| Lyophilized *S. cerevissae* | 75 mg |
| *Latobacillus* CNCM I-1225 dry mix | 50 mg |
| Glucidex IT 19 (maltodextrin powder) | QSP 500 mg |

The composition is administered to the individual in an amount of 2×500 mg daily, which provides a protective and preventive effect of the skin.

It should be understood that various changes' and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method of reducing effects of a skin disorder caused by solar radiation for an individual in need thereof, wherein the skin disorder is selected from the group consisting of erythema, inflammation, sun burn, photoageing, and combinations thereof, the method comprising:
orally administering to the individual a composition consisting of (i) live *Lactobacillus johnsonii* CNCM I-1225, (ii) at least one carotenoid selected from the group consisting of β-carotene, lycopene, and a combination of β-carotene and lycopene, and (iii) an orally acceptable carrier, wherein the composition is administered for at least one day in a quantity that provides $10^7$ to $10^{12}$ organisms of the live *Lactobacillus johnsonii* CNCM I-1225/day and a total amount of 5 to 30 mg of the at least one carotenoid/day.

2. The method of claim 1, wherein the composition is administered to the individual before exposure to ultraviolet radiation.

3. The method of claim 1, wherein the composition is administered to the individual during exposure to ultraviolet radiation.

4. The method of claim 1, wherein the composition is in a form of a tablet, and the orally acceptable carrier is a pharmaceutical carrier.

5. The method of claim 1, wherein the at least one carotenoid is a combination of β-carotene and lycopene.

6. The method of claim 1, wherein the skin disorder of the individual comprises erythema.

7. The method of claim 1, wherein the skin disorder of the individual comprises inflammation.

8. The method of claim 1, wherein the skin disorder of the individual comprises sun burn.

9. The method of claim 1, wherein the skin disorder of the individual comprises photoageing.

* * * * *